US011793963B2

(12) United States Patent
Moriarty

(10) Patent No.: US 11,793,963 B2
(45) Date of Patent: Oct. 24, 2023

(54) AMBULATORY TUBE SUPPORT FOR ENDOTRACHEAL TUBING

(71) Applicant: Tubetamer, LLC, Valley Center, CA (US)

(72) Inventor: Douglas Moriarty, Valley Center, CA (US)

(73) Assignee: TUBETAMER, LLC, Valley Center, CA (US)

( * ) Notice: Subject to any disclaimer, the term of this patent is extended or adjusted under 35 U.S.C. 154(b) by 262 days.

(21) Appl. No.: 17/152,408

(22) Filed: Jan. 19, 2021

(65) Prior Publication Data

US 2022/0226592 A1 Jul. 21, 2022

(51) Int. Cl.
*A61M 16/04* (2006.01)

(52) U.S. Cl.
CPC .... *A61M 16/0488* (2013.01); *A61M 16/0463* (2013.01)

(58) Field of Classification Search
CPC .......... A61M 16/0463; A61M 16/0488; A61M 16/0497; A61M 25/02; A61M 2025/022
See application file for complete search history.

(56) References Cited

U.S. PATENT DOCUMENTS

| | | | |
|---|---|---|---|
| 3,774,616 A | 11/1973 | White et al. | |
| 3,946,742 A | 3/1976 | Eross | |
| 4,774,944 A * | 10/1988 | Mischinski | ....... A61M 16/0488 128/DIG. 26 |
| 5,402,776 A | 4/1995 | Islava | |
| 5,551,421 A * | 9/1996 | Noureldin | ......... A61M 16/0488 604/179 |
| 5,806,516 A * | 9/1998 | Beattie | .............. A61M 16/0488 128/207.14 |
| 6,067,985 A | 5/2000 | Islava | |
| 6,336,457 B1 | 1/2002 | Hudson | |
| 6,634,359 B1 | 10/2003 | Rudy | |
| 8,156,934 B2 | 4/2012 | Trodler | |
| 8,636,008 B2 | 1/2014 | Flory | |
| 9,308,340 B2 | 4/2016 | Bond | |
| D834,185 S | 11/2018 | Molden | |

(Continued)

OTHER PUBLICATIONS

International Search Report and Written Opinion of the International Searching Authority for PCT Application No. PCT/US2022/011696 dated Mar. 24, 2022.

*Primary Examiner* — Colin W Stuart
*Assistant Examiner* — Matthew D Ziegler
(74) *Attorney, Agent, or Firm* — Charles F. Reidelbach, Jr.

(57) ABSTRACT

An ambulatory tube support and aligner for rapidly securing an endotracheal tube to an airway of a patient includes a support body, a fastener, and a compressible material. The support body has opposed inner and outer surfaces and includes a maxilla portion, a mandible portion, and two opposing end portions. The two opposing end portions individually connect the upper portion to the lower portion and define a perimeter of an opening. The opening is configured to overlay the mouth of the patient when the support body is secured to the patient. The fastener has a movable portion rotatively coupled to a fixed portion. A single rotation of the movable portion of the fastener causes the compressible material to secure the endotracheal tube at one end of the opening to provide an unobstructed view of the patient's mouth.

16 Claims, 3 Drawing Sheets

(56) References Cited

U.S. PATENT DOCUMENTS

2011/0240034 A1* 10/2011 Ciccone ............ A61M 16/0493
128/207.17
2016/0361509 A1    12/2016 Blessing
2021/0275767 A1     9/2021 Ferrandiz Catalan et al.

* cited by examiner

AMBULATORY TUBE SUPPORT FOR ENDOTRACHEAL TUBING

FIELD OF THE INVENTION

The present disclosure concerns an ambulatory tube support and aligner for securing an endotracheal tube to an airway of a patient. More particularly, the ambulatory aligner is configured for very rapid use and to allow viewing of the airway to assure proper alignment of the endotracheal tube.

BACKGROUND

During emergency ambulatory activities there is often a need for a tracheal tube to be placed in a patient airway. A key challenge is to secure the tracheal tube very quickly but also to be able to visually monitor placement of the tube.

SUMMARY

Figure 1:
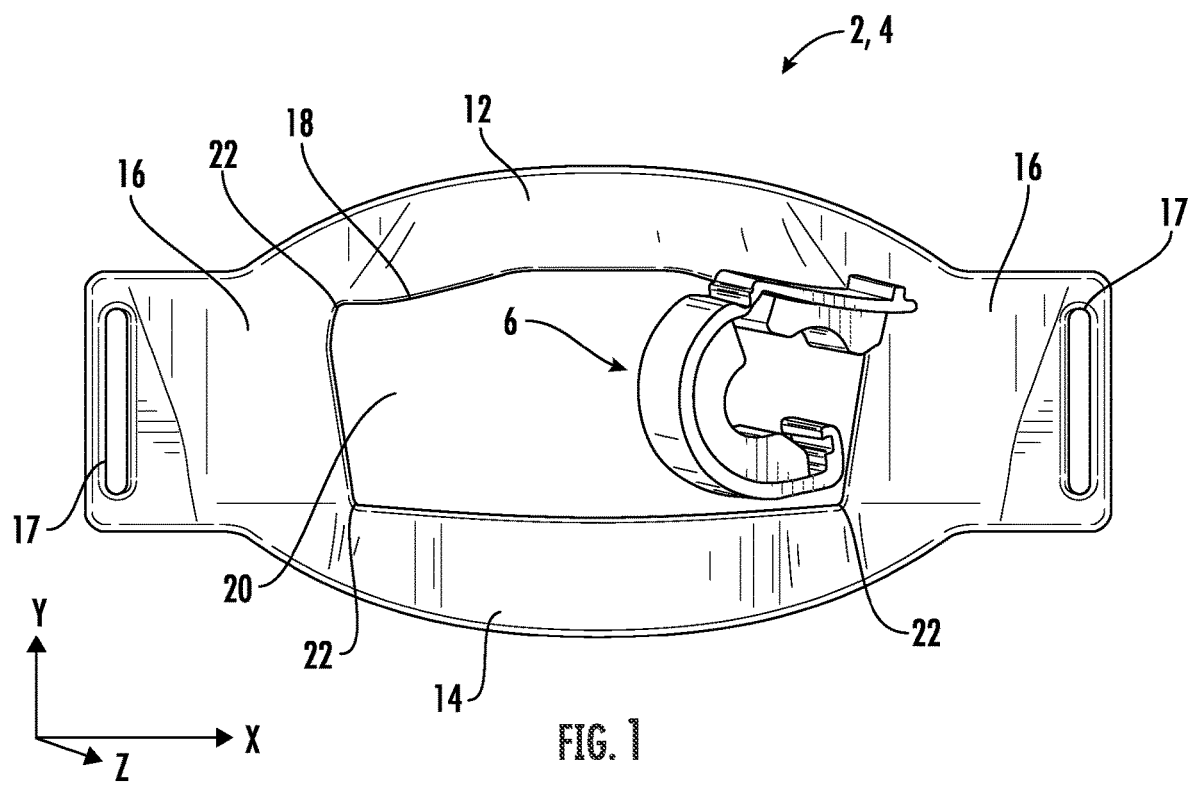
FIG. 1 is a front view of an embodiment of an ambulatory tube support structure.

In a first aspect of the disclosure, an ambulatory aligner for rapidly securing an endotracheal tube to an airway of a patient includes a support body, a fastener, and a compressible material. The support body has opposed inner and outer surfaces and includes a maxilla portion, a mandible portion, and two opposing end portions. The maxilla portion is configured to conform the inner surface to a maxilla side of a mouth of the patient. The mandible portion is configured to conform the inner surface to a mandible side of the mouth of the patient. The two opposing end portions individually connect the upper portion to the lower portion and define a perimeter of an opening. The opening is configured to overlay the mouth of the patient when the support body is secured to the patient. The fastener has a movable portion rotatively coupled to a fixed portion. The fixed portion is coupled to the support body. The movable portion has a concave surface and a lip. The compressible material is preferably disposed upon the fixed portion and concave surface of the fastener. Upon rotation of the movable portion with respect to the fixed portion of the fastener, the compressible material is configured to engage the endotracheal tube while the lip is configured to latch onto the fixed portion of the fastener. This engagement maintains a position of the endotracheal tube at an end of the opening proximate to one of the opposing end portions to provide an unobstructed view of a central region of the mouth of the patient.

This ambulatory aligner is advantageous for an emergency technician because it is very fast and simple to use. Unlike prior designs, the fastener is fixed in position and requires no adjustments which would tend to cost precious time during an emergency. Moreover, the movable portion of the fastener can be moved with one hand of an emergency technician from an unlatched configuration to a latched configuration with a single rotation of less than 100 degrees. This locates and secures the tracheal tube in the patient's airway at an optimal location very quickly with little or no chance of error. The use of the compressible material partly enables such a simple fastener because it widens a tolerance requirement of closure. Without the compressible material, a more complex ratchet or other design would be required and would slow down and complicate use of the ambulatory aligner.

This ambulatory aligner allows the emergency technician to view the tracheal tube while the patient is being transported. This is important because the shaking and transport of the patient can cause the tube to shift in location. With the central part of the opening viewable over the patient's mouth, the emergency technician can quickly identify and correct any misalignment or misplacement of the tracheal tube and to ensure patency or quickly visualize extubation of the endotracheal tube.

In one implementation, the support body has a material thickness in a range of 1-3 millimeters or about 2 millimeters. The thickness allows for structural integrity and alignment while facilitating conformance of the maxilla portion to the maxilla side of the patient mouth and the mandible portion to the mandible side of the patient mouth. The support body also has a curvature that further facilitates such conformance.

In another implementation, the opening has a major axis extending between the two end portions. The fixed portion of the fastener is coupled to the support body along an edge of the opening and along the major axis. The fixed portion has two opposed ends including a first end adjacent to a corner of the opening and a second end having a hinge coupled to the movable portion. The movable portion curves from the hinge at one end to the lip at the other end. The lip is configured to latch on to the first end of the fixed portion adjacent to the corner of the opening. The fixed portion of the fastener is coupled to the support body along an edge of the maxilla portion.

DETAILED DESCRIPTION OF THE PREFERRED EMBODIMENTS

FIG. 1 is a frontal isometric view of an embodiment of an ambulatory aligner 2. In describing portions of ambulatory aligner, mutually perpendicular axes X, Y, and Z can be used. Ambulatory aligner 2 includes a support body 4 and a fastener 6. The support body 4 includes a maxilla portion 12, a mandible portion 14, and two opposed end portions 16 that individually connect the maxilla portion 12 to the mandible portion 14. The end portions 16 individually define elongate openings 17 for allowing the use of a strap (not shown) for mounting the support body 4 to the patient's face.

Figure 2:
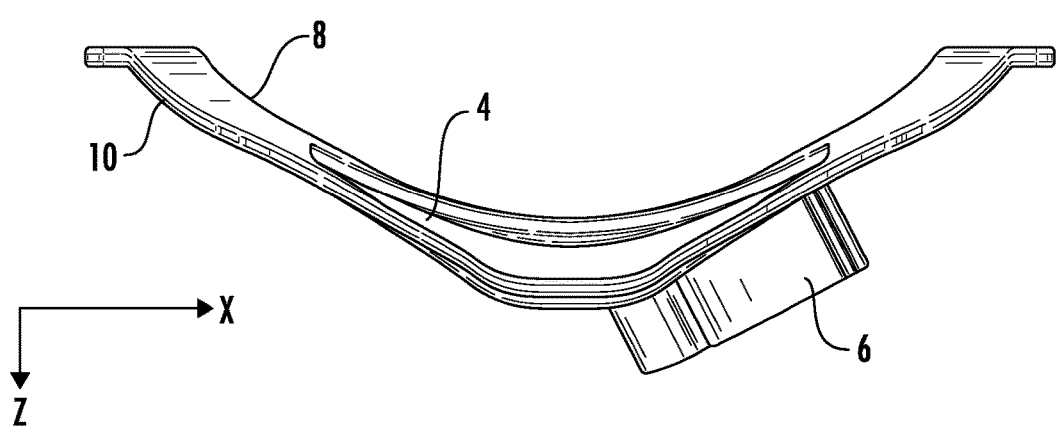
FIG. 2 is a top view of an embodiment of an ambulatory tube support structure.

FIG. 2 is an upper isometric view of the support body 4 and fastener 6. The support body 4 has opposed inner 8 and outer 10 surfaces. When in use, the inner surface 8 is supported upon a patient's face.

The maxilla portion 12 has a curvature of inner surface 8 to partially conform to a maxilla side of a patient's mouth. The mandible portion 14 has a curvature of inner surface 8 to partially conform to a mandible portion of a patient's mouth. The support body 4 has a degree of flexibility to facilitate the conformance. The support body 4 can have a thickness in a range of about 1 to 3 millimeters. In an illustrative embodiment, the thickness is about 2 millimeters. In an illustrative embodiment, the support body 4 and fastener 6 are integrally formed of polypropylene by injection molding.

The support body 4 defines a closed perimeter 18 (an inside edge 18) of an opening 20. Opening 20 has a major axis along X and a minor axis along Y. Opening 20 also defines four corners 22.

Figure 4:
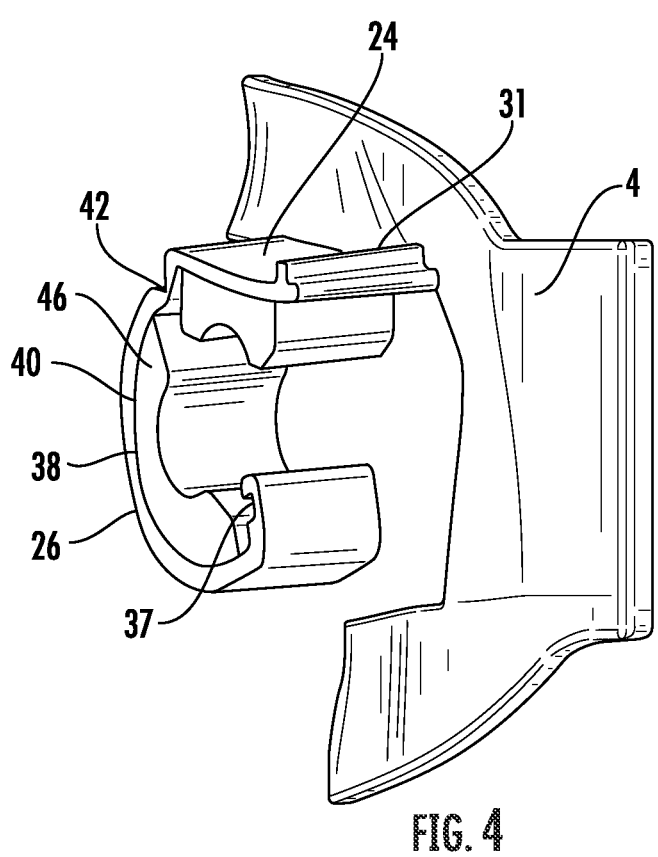
FIG. 4 is an isometric and frontal view of a portion of an ambulatory tube support structure.

As seen from FIG. 2, the fastener 6 extends outward from the outer surface 10 of support body 4. FIG. 4 is an isometric side frontal view of the support body 4 with fastener 6. FIG. 4 is an isometric view of a portion of the support body 4 with the fastener 6.

Figure 3:
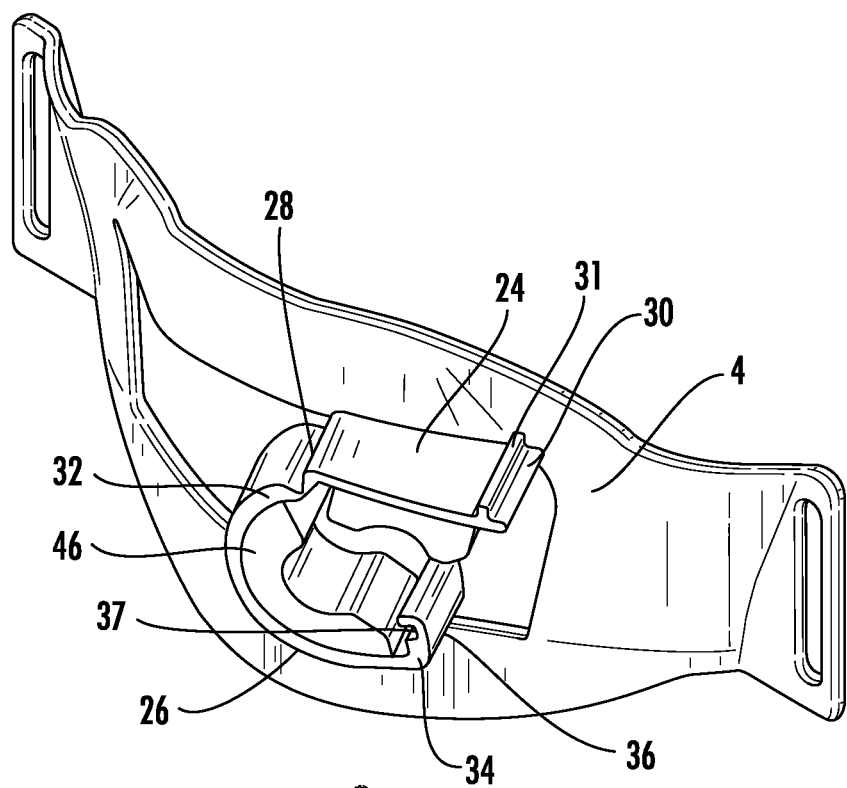
FIG. 3 is an isometric and frontal view of an embodiment of an ambulatory tube support structure.

The fastener 6 includes a fixed portion 24 and movable portion 26. The fixed portion 24 is attached to the support body 4 along the perimeter 18 of the opening 20. The fixed portion 24 includes a first end 28 and a second end 30 (FIG. 3). The movable portion 26 has a fixed end 32 and free end 34 with a lip 36. Between the fixed end 32 and the free end 34 is a curved portion 38 (FIG. 4) having a concave surface 40. A hinge 42 joins the first end 28 of the fixed portion 24 to the fixed end 32 of the movable portion 26.

The movable portion 26 is configured to rotate along the hinge 42 between an open configuration (shown in FIGS. 1, 3, and 4) to a closed configuration (FIGS. 5 and 6) in which the lip 36 is latched to the second end 30 of the fixed portion 24. In the closed configuration, the concave surface 40 is generally facing toward the fixed portion 24.

In the illustrative embodiment, the second end 30 includes an upstanding ridge 31 (FIGS. 3, 4). The lip 36 defines a groove 37. When the moveable portion 26 is rotated from the open configuration to the closed configuration, the ridge 31 is received into the groove 37 to latch the lip 36 to the second end 30.

Figure 5:
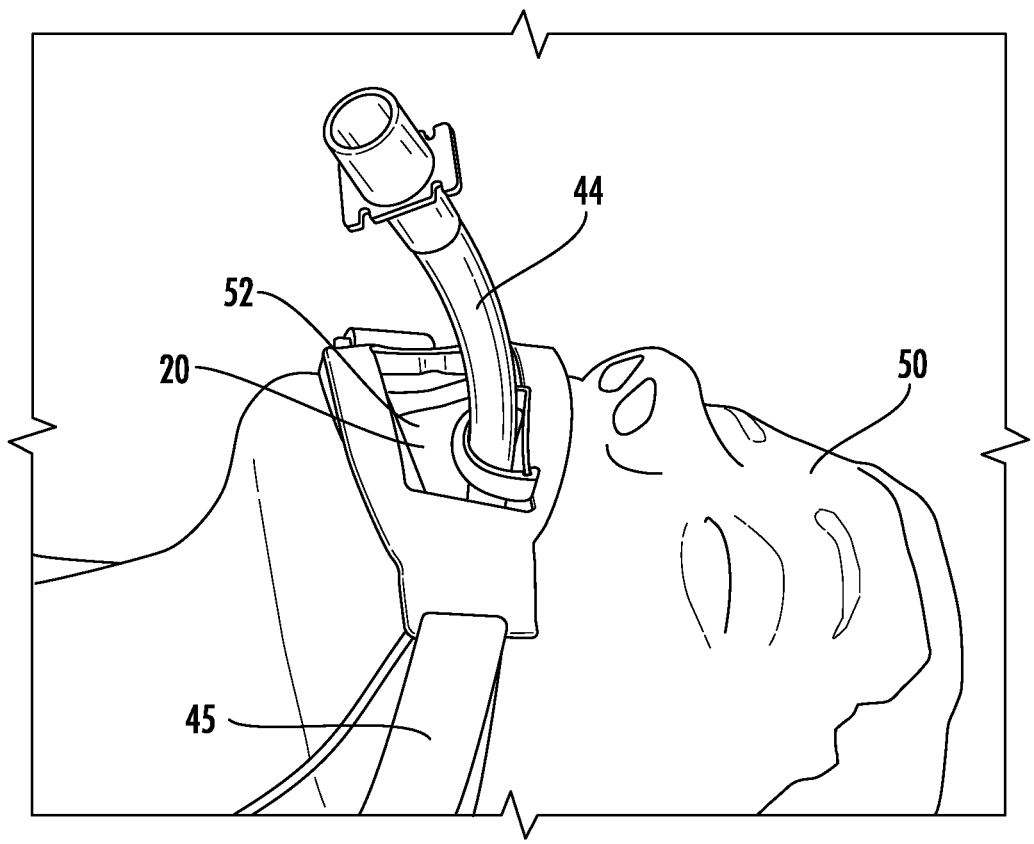
FIG. 5 is an isometric side view of an embodiment of an ambulatory tube support structure used on a model of a patient.

FIG. 5 is an illustrative view of the ambulatory aligner 2 securing and aligning a position of a tracheal tube 44 on a patient (model) 50. The tracheal tube 44 is secured by the fastener 6 proximate to a corner 22 of the opening 20. This allows the mouth 52 of the patient 50 to be visible through a central area of the opening 20. Also shown are straps 45 that secure the ambulatory aligner 2 to the patient 50.

Figure 6:
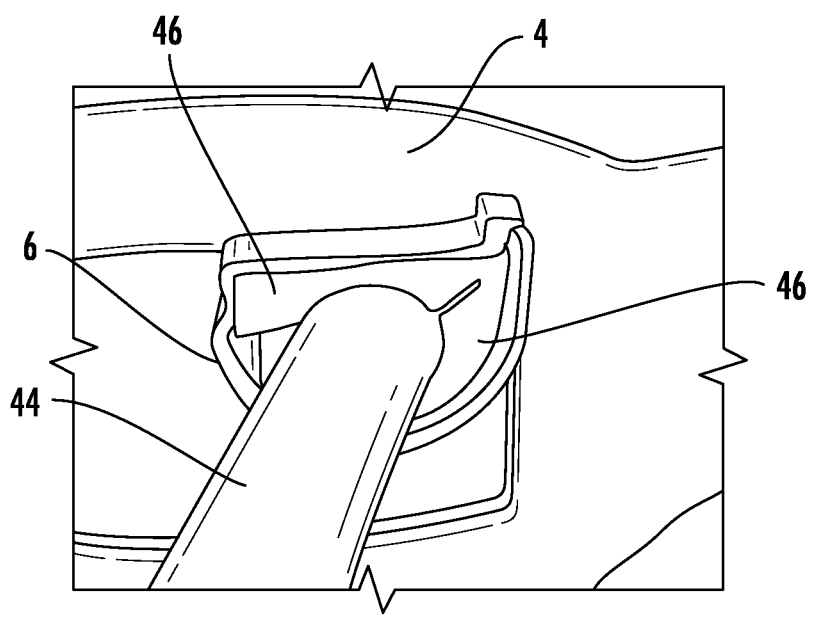
FIG. 6 is an isometric front view of a portion of an embodiment of an ambulatory tube support structure used on a model of a patient.

FIG. 6 is a close up isometric view of a portion of the support body 4 with the fastener 6 in closed configuration and clamping or securing the tracheal tube 44. A compressible material 46 (e.g., open or closed cell foam) is disposed between the fastener 6 and the tracheal tube 44. The compressible material 46 is between the tracheal tube 44 and the fixed portion 24. The compressible material 46 is between the concave surface 40 (or curved portion 38 or movable portion 26) and the tracheal tube 44.

Use of the compressible material 46 reduces a criticality of tolerances in the design. This is what enables a simple closure mechanism with a single latching lip 36 rather than more complicated ratchets that would otherwise be needed. The simplicity of this latching fastener 6 is what allows an emergency technician to quickly use this ambulatory aligner with a single hand when every second can be critical to the patient.

The specific embodiments and applications thereof described above are for illustrative purposes only and do not preclude modifications and variations encompassed by the scope of the following claims.

What is claimed:

1. An ambulatory aligner for rapidly securing an endotracheal tube to an airway of a patient comprising:
    a support body having opposed inner and outer surfaces and including:
    a maxilla portion configured to conform the inner surface to a maxilla side of a mouth of the patient;
    a mandible portion configured to conform the inner surface to a mandible side of the mouth of the patient; and
    two opposing end portions that individually connect the maxilla portion to the mandible portion to define and enclose a perimeter of one opening configured to overlay at least a central portion of the mouth of the patient when the support body is secured to the patient; and
    a fastener having a movable portion that is rotatively coupled to a fixed portion, the fixed portion is permanently affixed to the support body at an end of the opening proximate to one of the opposing end portions, the movable portion having concave surface and a lip; and
    a compressible material disposed upon the fixed portion and concave surface of the fastener; and,
    upon rotation of the movable portion with respect to the fixed portion of the fastener, the compressible material is configured to engage the endotracheal tube while the lip is configured to latch onto the fixed portion of the fastener to maintain a position of the endotracheal tube at an end of the opening proximate to one of the opposing end portions to provide an unobstructed view through the opening over the central portion of the mouth of the patient thereby providing visual confirmation of airway patency.

2. The ambulatory aligner of claim 1 wherein the support body has a thickness between the inner and outer surfaces in a range of one to three millimeters.

3. The ambulatory aligner of claim 1 wherein the opening has a major axis extending between the two opposing end portions, the fixed portion of the fastener is coupled to the support body along an edge of the opening and along the major axis.

4. The ambulatory aligner of claim 3 wherein the fixed portion has two opposed ends including a first end adjacent to a corner of the opening and a second end having a hinge coupled to the movable portion.

5. The ambulatory aligner of claim 4 wherein movable portion curves from the hinge to the lip.

6. The ambulatory aligner of claim 4, the lip is configured to latch on to the first end adjacent to the corner of the opening.

7. The ambulatory aligner of claim 1 wherein the fixed portion of the fastener is coupled to the support body along an edge of the maxilla portion.

8. The ambulatory aligner of claim 1 wherein the two opposing end portions have elongate openings for receiving straps for coupling the support body to a head of the patient.

9. The ambulatory aligner of claim 1 wherein the fixed portion of the fastener is coupled to the support body along an edge of the maxilla portion.

10. An ambulatory aligner for rapidly securing an endotracheal tube to an airway of a patient comprising:
    a support body having opposed inner and outer surfaces, the support body defining and enclosing a closed perimeter of an opening configured to overlay at least a central portion of a mouth of the patient when the support body is secured to the patient, the opening having a major axis along an X-axis, the support body including:
    a maxilla portion having a curved shape and flexibility to conform the inner surface to a maxilla side of a mouth of the patient;

a mandible portion having a curved shape and flexibility to conform the inner surface to a mandible side of the mouth of the patient; and two opposing end portions that individually couple the maxilla portion to the mandible portion;

a fastener having a fixed portion and a movable portion, the fixed portion is permanently affixed to the support body at an end of the opening proximate to one of the opposing end portions and having a first end with a hinge and a second end opposite to the first end, the movable portion having a fixed end coupled to the hinge and a free end with a lip, the movable portion having a curved portion coupling the fixed end to the lip, the movable portion defines a concave surface;

a compressible material disposed upon the concave surface and upon the fixed portion; rotation of the movable portion from an open configuration to a closed configuration moves the lip from an unlatched configuration to a latched configuration with the lip latched to the second end of the fixed portion with the concave surface generally facing the fixed portion and the compressible material securing the endotracheal tube proximate to one end of the opening with respect to the X-axis to provide an unobstructed view through the opening over the mouth of the patient thereby providing visual confirmation of airway patency.

11. The ambulatory aligner of claim 10 wherein the support body has a thickness between the inner and outer surfaces in a range of one to three millimeters.

12. The ambulatory aligner of claim 10 wherein the fixed portion is coupled to the support body along an edge of the opening and along the major axis.

13. The ambulatory aligner of claim 12 wherein the second end of the fixed portion is proximate to a corner of the opening.

14. The ambulatory aligner of claim 13 wherein the fixed portion of the fastener is coupled to the support body along an edge of the maxilla portion.

15. The ambulatory aligner of claim 10 wherein the fixed portion of the fastener is coupled to the support body along an edge of the maxilla portion.

16. The ambulatory aligner of claim 10 wherein a single rotation of less than 100 degrees moves the movable portion from an unlatched configuration to a latched configuration.

* * * * *